United States Patent [19]

Axelson, Jr.

[11] Patent Number: 5,658,292

[45] Date of Patent: Aug. 19, 1997

[54] INSTRUMENTATION FOR PREPARING A DISTAL FEMUR

[75] Inventor: Stuart L. Axelson, Jr., Rahway, N.J.

[73] Assignee: Pfizer Hospital Products Group, Inc., New York, N.Y.

[21] Appl. No.: 408,508

[22] Filed: Mar. 22, 1995

Related U.S. Application Data

[63] Continuation of Ser. No. 920,081, Jul. 27, 1992, Pat. No. 5,417,695.
[51] Int. Cl.⁶ .............................................. A61B 17/00
[52] U.S. Cl. .............................. 606/86; 606/88; 606/80
[58] Field of Search ................................ 606/53, 60, 62, 606/64, 67, 69, 71, 74, 79, 80, 86, 87, 88, 89, 96, 90, 104; 623/20

[56] References Cited

U.S. PATENT DOCUMENTS

| | | | |
|---|---|---|---|
| 4,325,373 | 4/1982 | Slivenko et al. | 606/80 X |
| 4,467,801 | 8/1984 | Whiteside | 606/80 X |
| 4,474,177 | 10/1984 | Whiteside | 606/88 X |
| 4,703,751 | 11/1987 | Pohl | 606/62 |
| 4,721,104 | 1/1988 | Kaufman et al. | 606/88 |
| 4,827,919 | 5/1989 | Barbarito et al. | 606/86 X |
| 5,047,032 | 9/1991 | Jellicoe | 606/83 |
| 5,098,436 | 3/1992 | Ferrante et al. | 606/53 X |
| 5,176,684 | 1/1993 | Ferrante et al. | 606/86 |

Primary Examiner—Sam Rimell
Attorney, Agent, or Firm—Peter C. Richardson; Lawrence C. Akers; Raymond W. Augustin

[57] ABSTRACT

A method and apparatus for preparing a planar surface on the distal femur prior to implantation of a femoral knee prosthesis has a femoral plate with an opening therein for exposing both condyles of the femur. A guide with a central aperture is used to align the femoral plate on the distal femur. The guide is releasably secured to the femoral plate and an intramedullary guide rod is placed through the aperture therein and into the intramedullary canal of the femur. After alignment with the intramedullary canal, the femoral plate is pinned to the femur and the rod and guide are removed. A milling guide having two bores, one adjacent each condyle, is then placed on the femoral plate and an end mill is used to mill a planar surface on at least one of the condyles.

4 Claims, 5 Drawing Sheets

INSTRUMENTATION FOR PREPARING A DISTAL FEMUR

This application is a continuation of U.S. application Ser. No. 07/920,081, filed Jul. 27, 1992, now U.S. Pat. No. 5,417,695.

BACKGROUND OF THE INVENTION

1. Field of the Invention

This invention relates to a method and apparatus for preparing a distal surface of a human femur. More particularly, it relates to a set of instruments and a method for their use to prepare the surface of the femur to receive a distal femoral prosthesis.

2. Description of the Prior Art

Various types of instruments and methods have been developed to enable a surgeon to affix a distal femoral knee prosthesis to a human femur. Since the purpose for affixing such a prosthesis is to restore the patient's ability to walk after disease or other traumatic causes have impaired that ability, it is important that the prosthesis be attached to the femur in a manner that will approximate as closely as possible the natural condyles which the prosthesis is replacing.

It is a common practice to use the long central axis of the femur as a guide in determining the manner in which the distal femoral surfaces should be shaped to receive a properly aligned distal femoral prosthesis. Using the long central axis of the femur as a guide, a planar distal cut is first made on the distal femur and then the guide is removed and additional instrumentation utilizes the planar distal surface as a reference from which to cut anterior and posterior cuts, followed by anterior and posterior chamfer cuts.

Patents showing such a method or methods similar thereto are U.S. Pat. Nos. 4,474,177 and 4,721,104. The former patent relates to a series of instruments for preparing the distal femur in which an angled alignment guide is used to index a plateau planar which is used to prepare the planar distal surface of the femur. The latter patent relates to a surgical apparatus for preparing the intracondylar area of the distal femur.

U.S. Pat. No. 5,047,032 relates to a surgical instrument designed to produce a planar distal femoral surface. A router or side cutting drill is used to form the surface. Another patent which relates to the preparation of the distal femur is U.S. Pat. No. 4,787,383, in which a saw is used to make the planar femoral cut. A saw guide is also disclosed.

SUMMARY OF THE INVENTION

It is an object of this invention to provide an apparatus for forming planar surfaces on the medial and lateral condyles of the distal femur which is simple in design.

It is another object of the invention to provide a method for using the apparatus which method is simple to perform and therefore saves time during surgery.

These and other objects are achieved by an apparatus for milling a planar distal femoral surface which surface contains at least one of the medial and lateral condyles of a femur. The apparatus is initially located by use of an intramedullary rod extending into the intramedullary canal of the femur. The guide rod aligns a guide block which in turn aligns a ring-like femoral plate having a generally oblong opening therein which exposes both the medial and distal condyles when the plate is secured to the femur. The plate is secured to the medial and lateral surfaces of the distal femur by drill pins. The femoral bushing guide block fits within the generally oblong opening in the femoral plate and has a central hole therein angled laterally at an angle of about 8° from a direction perpendicular to the face of the femoral plate. Once the femoral plate is aligned, the guide block, bushing and rod are removed and a milling guide block having a pair of cylindrical medial and lateral guide bores therein adjacent the respective medial and lateral condyles is placed thereon. The milling guide block is inserted into the oblong opening in the femoral plate after the femoral plate is firmly secured to the femur and the femoral bushing and guide block which hold the intramedullary rod is removed therefrom. The distal milling guide has a generally oblong shape which is snugly received within the oblong opening in the femoral plate. A cylindrical end mill cutter is inserted in at least one of the medial and lateral bores for milling said medial or lateral condyles. The end mill cutter has a bottom surface with at least two blades aligned to cut a flat surface. The milling of only one condyle would be required in a uni-condylar knee replacement wherein a prosthesis is implanted only on one of the condyles.

The milling guide block has a circumferential rim thereon for engaging a flange on the distal end mill cutter to permit milling of the condyles to a predetermined depth. This depth can be varied by placing a ring-like spacer between the flange on the distal end mill cutter and the rim on the milling guide block which surrounds the opening in the milling guide block.

These and other objects and advantages of the present invention will become apparent from the following description of the accompanying drawings, which discloses one embodiment of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
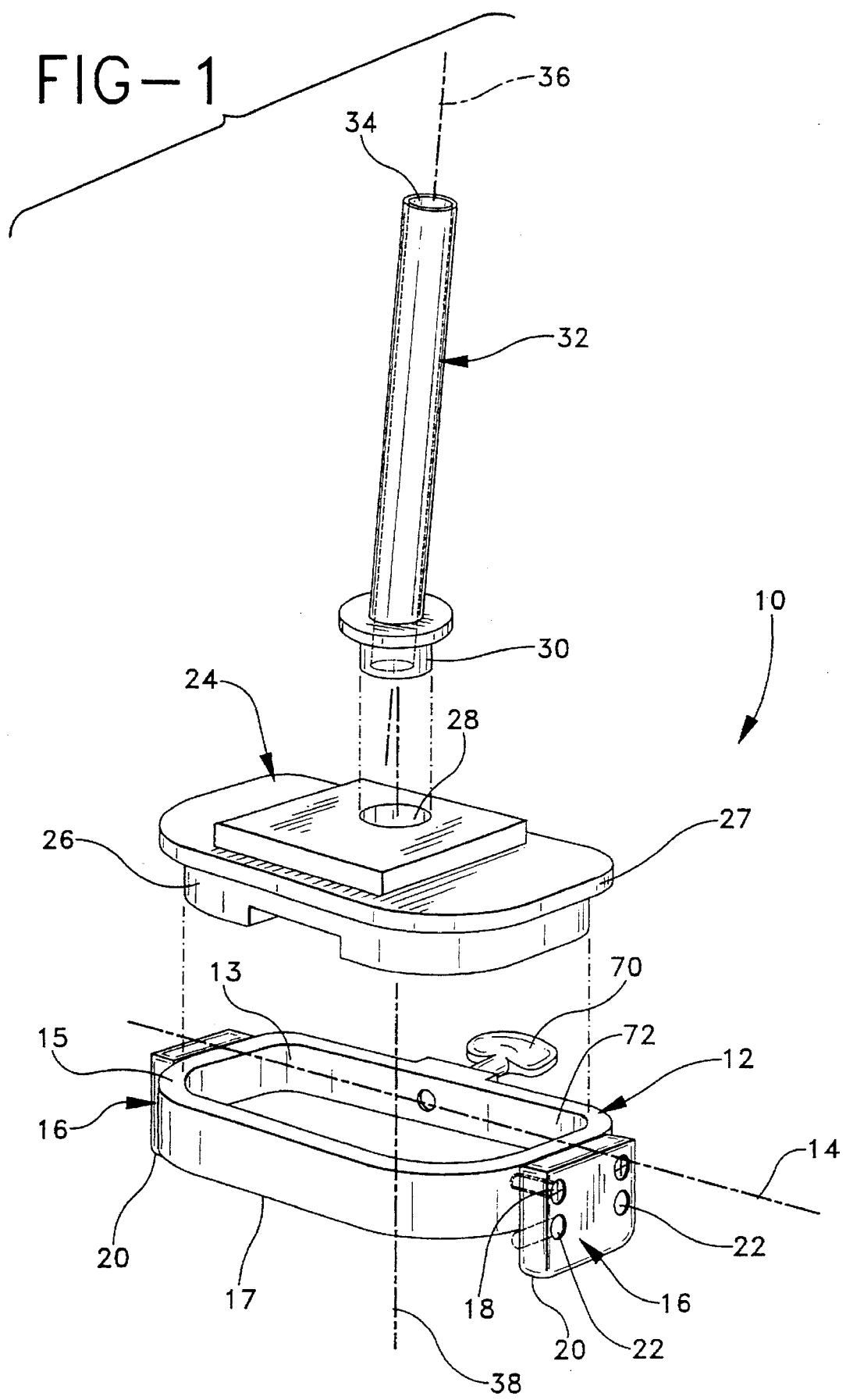
FIG. 1 is an exploded isometric view of the distal femoral plate of the present invention including the bushing block and bushing for the alignment thereof.

Referring to FIG. 1 there is shown a distal femoral plate 10 which, in the preferred embodiment, is in the form of an oval ring-shaped body 12 having a longitudinal axis 14. Body 12 has a top surface 15, a bottom surface 17 and an inner surface in the form of wall 13. Body 12 has a pair of flanges 16 at each end thereof which flanges are centered with respect to longitudinal axis 14 and, in the preferred embodiment, coupled to body 12 by screws 18.

Figure 2:
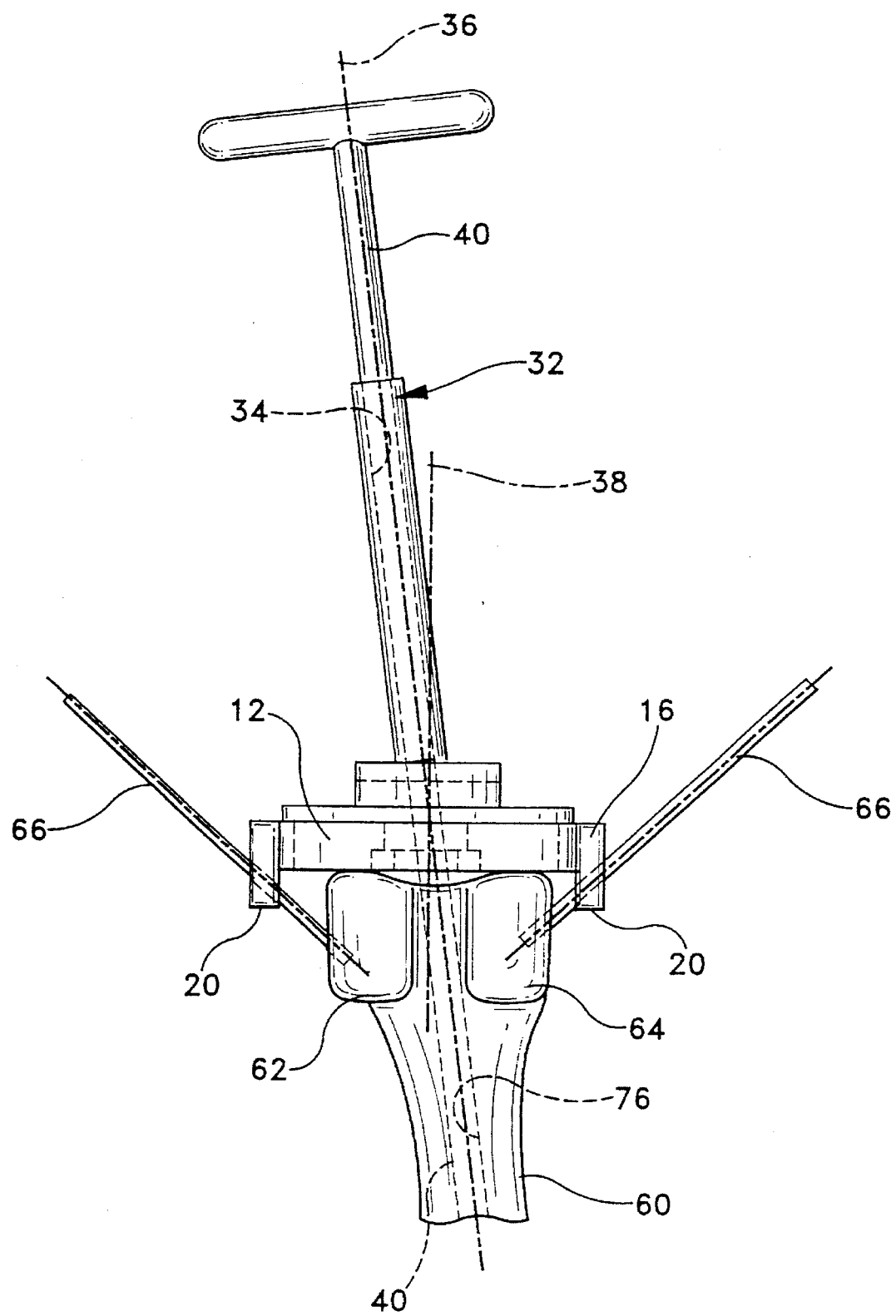
FIG. 2 is an elevation view showing the distal femoral plate of FIG. 1 in alignment on and connected to the distal femur.

As seen in FIG. 2, the length of ring-shaped body 12 along longitudinal axis 14 in the preferred embodiment is selected to accommodate both the medial and lateral condyles 62, 64 of the distal femur 60. Thus, the distance between flanges 16 along axis 14 is sufficient so that the bottom surface 20 of each flange 16 extends proximally beyond the distal surface of the distal condyles. A pair of pin holes 22 are formed in flange 16 and are adapted to receive pins 66 which will be discussed in greater detail below. In the preferred embodiment holes 22 are angled inwardly toward the proximal end of femur 60. An axis 38 extending in a direction perpendicular to a plane containing top surface 15 of body 12 is located along axis 14 intermediate flanges 16.

Again referring to FIGS. 1 and 2, there is shown a femoral bushing guide block 24 having a flange 27 forming a stop surface thereon. A generally oblong wall 26 extends proximally from stop surface 27 of block 24. Wall 26 is shaped to be slidably received within interior surface 13 of ring 12. The lower surface of flange 27 engages top surface 15 of femoral plate 10 to limit the penetration of the guide block 24 therein. Femoral bushing guide block 24 also includes a central bore 28 coaxial with axis 38 and sized to receive cylindrical end 30 of an intramedullary rod bushing 32. Bushing 32 includes a bore 34 for receiving an intramedullary guide rod 40. Bore 34 in intramedullary rod bushing 32 extends along the longitudinal axis 36 which is angularly offset from bore 28 within femoral bushing guide block 26. In the preferred embodiment this offset is 5°, 7° or 9°.

In the preferred embodiment, intramedullary rod bushing 32 is made separate from femoral bushing guide blocks so that the angle between axis 36 and 38 may be varied, from 5° to 9° by a series of bushings 32, each having an axis 36 varying in 1° or 2° increments with respect to axis 38.

Figure 3:
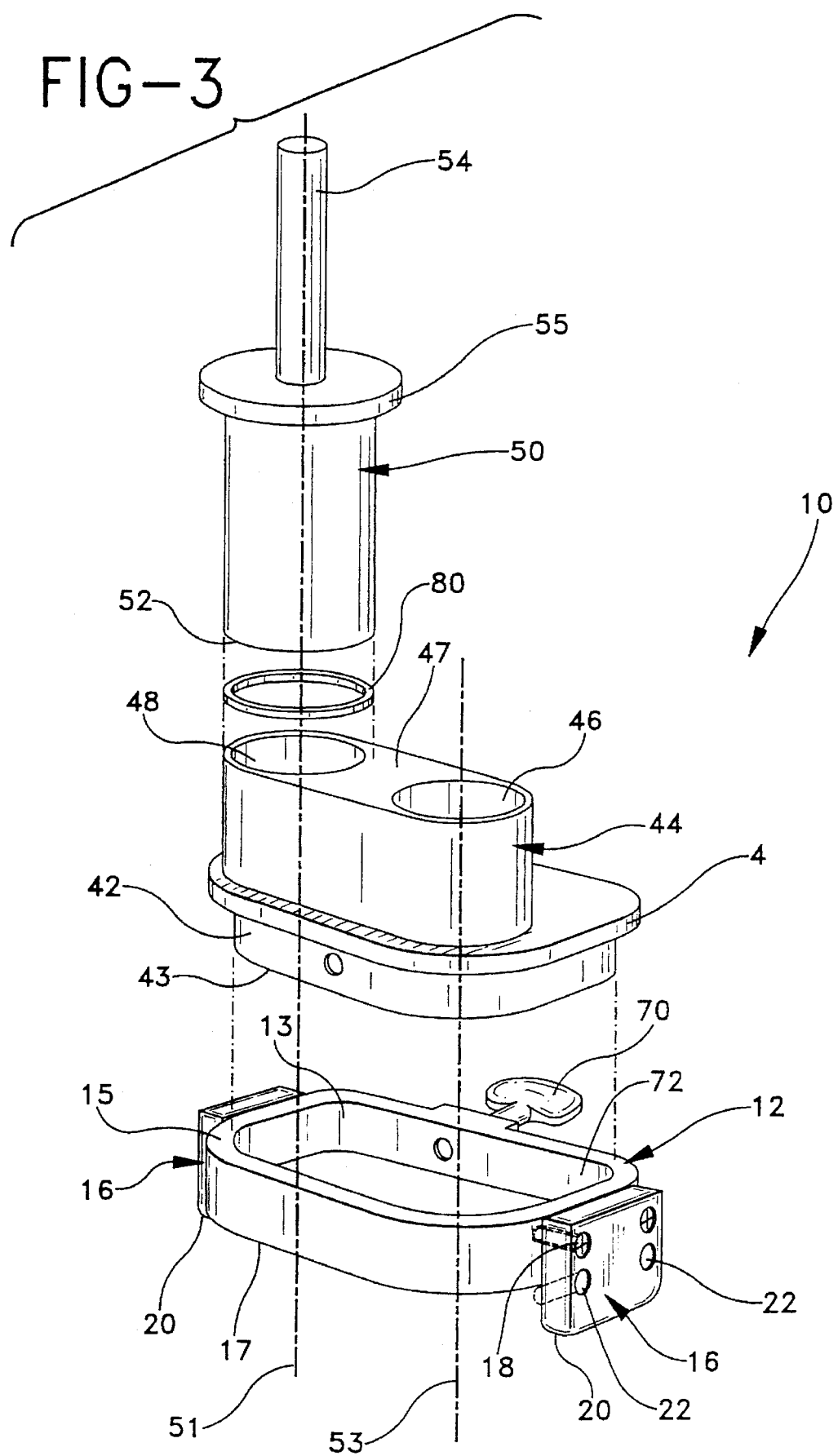
FIG. 3 is an exploded isometric view of the end mill and milling guide of the present invention prior to being inserted into the distal femoral plate.

Referring to FIG. 3 there is shown a distal milling block 44 and femoral distal plate 10 as previously described. Milling guide 44 is designed to cooperate with the distal femoral plate 10 in a manner similar to bushing guide block 24. Surface 13 of ring 12 of plate 10 receives a proximally extending wall 42 of distal milling guide 44. Similar to guide block 24, milling guide 44 has a stop surface 41 which engages surface 15 of femoral plate 10. Distal milling guide 44 includes a pair of bores 46 and 48 respectively, which have longitudinal axes 51, 53 which are parallel with axis 38. In the preferred embodiment, the axes 51, 53 of bores 46 and 48 are offset with respect to a plane containing the axis 14 of distal femoral plate 10. The reason for this offset will be described in more detail below. The diameter of both bores 46 and 48 is sized to receive a distal end mill cutter 50 shown in FIGS. 3 and 4. End mill cutter 50 includes a milling surface 52 and a drive shaft 54 adapted to be connected to a suitable rotating power source. When inserted in either bore 46 or 48, the axis of drive shaft 54 is aligned with axes 51, 53. Spacers 80 may be provided to adjust the depth that surface 52 extends beyond the bottom surface 43 of wall 42 of guide 44 (i.e. to space flange 55 from surface 47 of guide 44).

Figure 4:
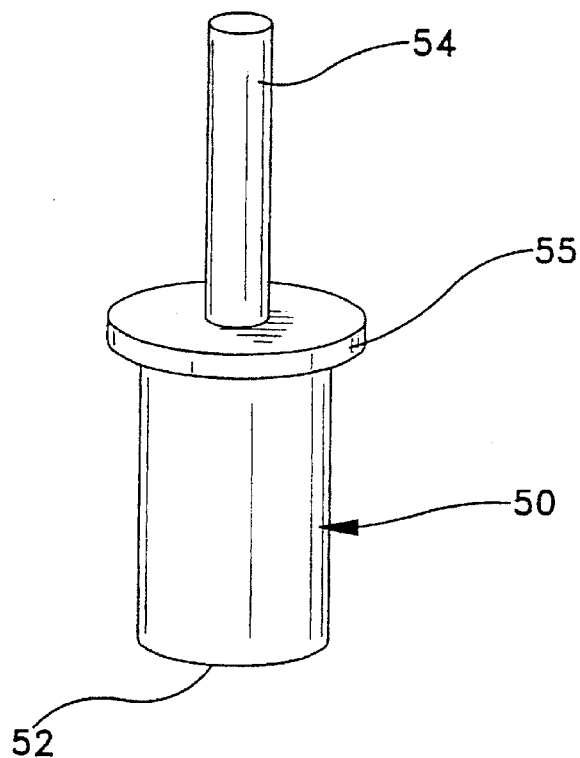
FIG. 4 is an elevation view of the end mill of FIG. 3.
Figure 5:
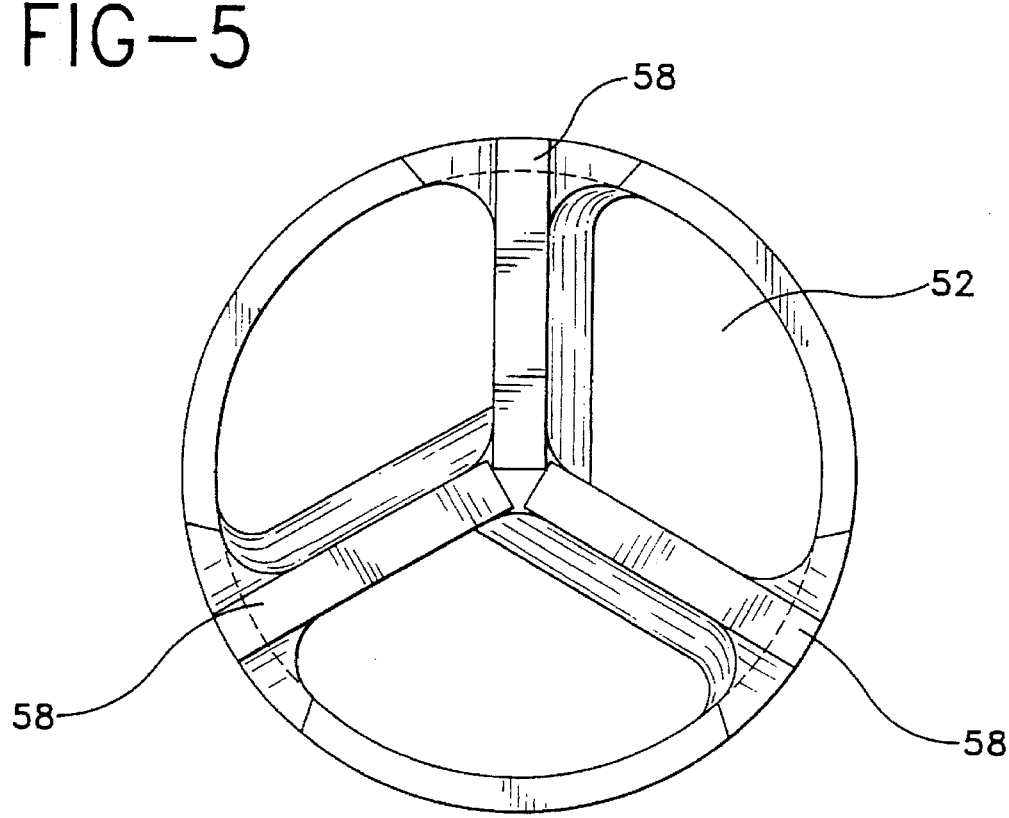
FIG. 5 is a bottom view of the cutting surface of the end mill of FIG. 4.

Referring to FIGS. 4 and 5, it can be seen that surface 52 contains preferably three blades 58 for end milling a planar surface on the condyles of the distal femur. Two blades 58 or blades in excess of three may also be used.

Figure 6:
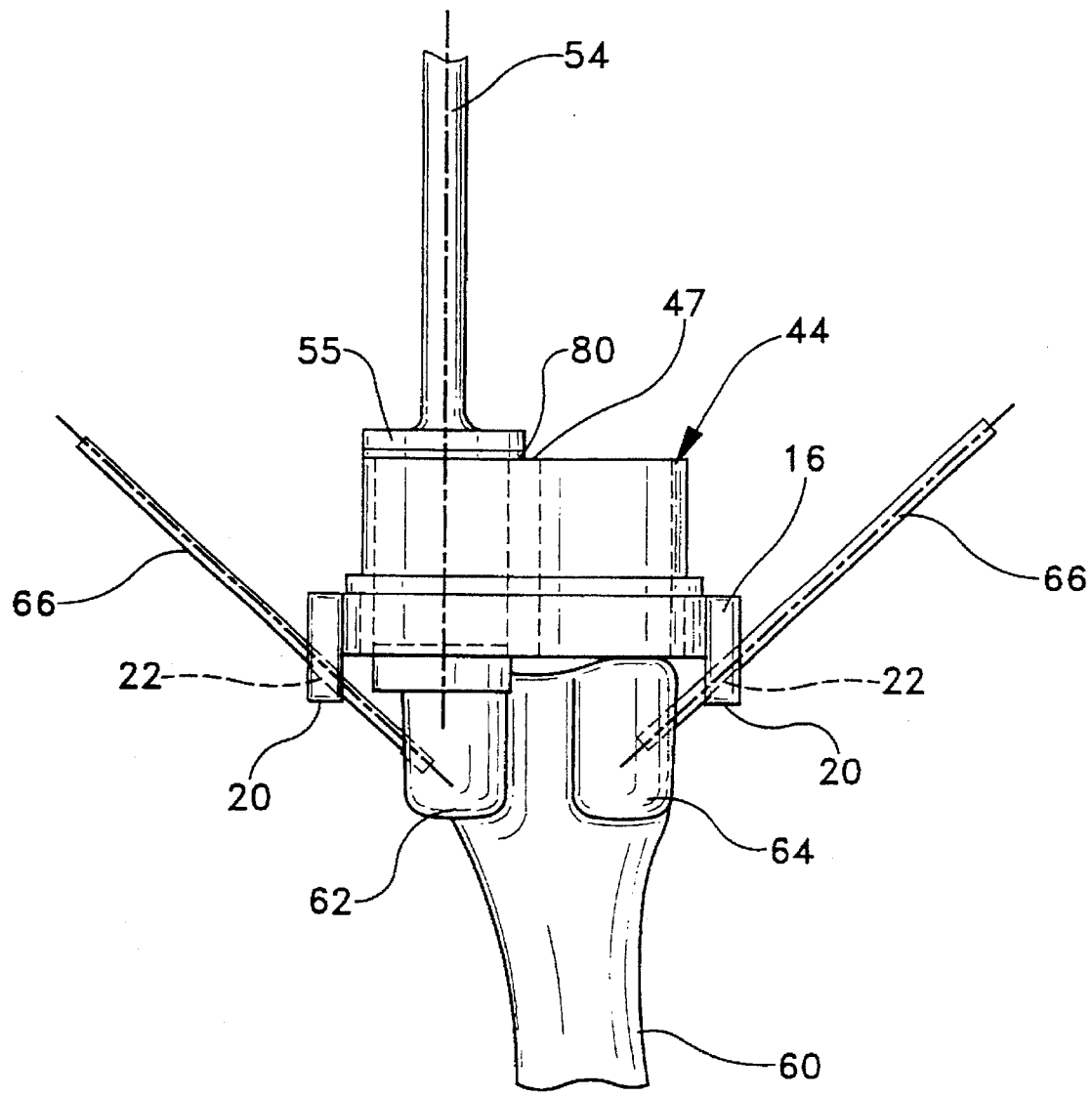
FIG. 6 is an elevation view of the distal femoral plate mounted on a femur with the components of FIG. 3 located therein.

Referring to FIG. 6 there is shown the femoral plate of the present invention mounted on a distal femur 60 with mill cutter 50 in its final position. FIG. 6 shows distal femur 60 including condyles 62 and 64 with femoral plate 10 held thereon by four pins 66. Spacer 80 is shown in place on surface 47 of guide 44, which spacer 80 in the preferred embodiment, is one millimeter thick. One or more spacers may be used to adjust the depth of the condylar planar cut made by end mill 50.

The method of preparing a distal femoral surface by milling the medial lateral condyles 62, 64 of a femur 60 with the apparatus of the present invention will now be described. First a femoral bushing guide block 24 with an appropriately angled guide bushing 32 mounted in bore 28 thereof is placed into the distal femoral plate 10 with wall 26 slidably received with surface 13 of body 12. In the preferred embodiment a thumb screw 70 may be used to lock guide block 24 into femoral plate 10. In addition, the angular offset between axis 36 and 38 may be any angle between 5° and 9° with a series of bushings 32 being provided which result in an angular offset of 5°, 7° or 9°.

After bushing 32, bushing guide block 24 and distal femoral plate 10 are assembled, intramedullary rod 40 is passed through bore 34 of the guide bushing 32 and into the medullary canal 76 of the femur 60. The assembly of distal femoral plate 10, guide bushing 24 and guide 32 are advanced distally on the rod 40 until contact is made with the prominent condyle 62, 64. Distal femoral plate 10 is then rotated so that a posterior wall 72 of surface 13 of plate 10 is parallel to a plane containing the posterior surface of the femoral condyles 62 and 64. Drill pins 66 are then placed through all four holes 22 of flange 16 and into the medial-lateral sides of the condyles. In the preferred embodiment, holes 22 are angled toward the proximal end of femur 60 so that the pins 66 contact the medial and lateral sides of the condyles away from the distal area where the milling is to take place.

Once the femoral plate 10 is fixed in position by pins 66, the femoral bushing guide block 24, intramedullary rod guide bushing 32 and intramedullary rod 40 are removed. At this point in the surgery, the distal milling guide 44 is placed into the distal femoral plate and locked therein with the anteriorly positioned thumb screw 70. Distal end mill 50 is then inserted into circular bore 46 or 48 of milling guide 44. End mill 50 includes a flange 55 which contacts surface 47 of milling guide 44 and determines the depth of penetration of cutting surface 52 into the condyles 62 or 64. In the preferred embodiment, the milling guide penetrates the condyle distally 10 mm, at which time flange 55 contacts surface 47, thereby limiting penetration. Cylindrical spacer 80 may be used to limit the depth of penetration. For example, a 1 mm thick spacer 80 would limit the penetration of surface 52 into the condyles to 9 mm when it is inserted between flange 55 and surface 47 of guide 44.

The circular holes 46 and 48 are off center with respect to a plane containing a longitudinal axis 14 and perpendicular to the plane defined by the surfaces 15 of femoral plate 10 (i.e. they are offset in the anterior-posterior direction with respect to a medial-lateral plane through the femur). This allows the surgeon to flip the milling guide 180° about axis 38 and the longitudinal axis of the femur and mill additional bone in the anterior-posterior plane if necessary to prepare a larger planar surface on the distal femoral condyles. Because the circular bores 46 and 48 are offset in the anterior-posterior direction, a generally oval cut can be made on the condyles.

With the use of the system described above, extremely accurate flat bone cuts are made on both condyles 62 and 64. As with most knee instrumentation systems and surgical methods used for the preparation of the distal femur for implantation of a prosthetic femoral knee component, all other bone cuts are indexed off this first distal planar surface on the femur. It is contemplated that these other cuts are made in any well known manner after using the instrumentation of the present invention.

While one example of the present invention has been described, it is obvious that many changes and modifications may be made thereunto, without departing from the spirit and scope of the invention.

I claim:

1. An apparatus for milling a distal femoral surface containing the medial and lateral condyles of a femur having an intramedullary canal, said apparatus comprising:

an alignment element for connection to the distal end of the femur, said alignment element exposing at least one of the condyles when said alignment element is secured to said distal femur;

means for aligning said alignment element with respect to the intramedullary canal;

means for securing said alignment element to said distal femur after being aligned;

a milling guide block coupled to said alignment element, said guide block having an outer surface engaging a positioning means on said alignment element and having at least one guide therein adjacent a respective medial and lateral condyles, said milling guide block having a stop surface thereon; and a cylindrical end mill cutter for insertion in and sliding engagement with said at least one medial and lateral guide in said guide block for milling said medial or lateral condyles, said end mill having a radially extending guide surface for engaging said stop surface on said guide block to permit milling of said condyles to a predetermined depth.

2. An apparatus for milling a distal femur as set forth in claim 1 further comprising at least one spacer for insertion between said guide surface on said end mill and said stop surface on said milling guide block to vary the predetermined depth of said milling of said condyles.

3. An apparatus for milling a distal femoral surface containing the medial and lateral condyles of a femur having an intramedullary canal, said apparatus comprising;

a femoral alignment plate for connection to the distal end of the femur, said alignment plate exposing at least one of the condyles when said plate is secured to said distal femur;

an intramedullary rod and alignment guide for aligning said femoral alignment plate with respect to the intramedullary canal of the femur;

bone pins for securing said femoral alignment plate to said distal femur after being aligned;

a milling guide block coupled to said femoral alignment plate, said guide block having an outer surface engaging a positioning surface on said femoral alignment plate and having at least one guide therein adjacent a respective medial and lateral condyle, said milling guide block having a stop surface thereon; and a cylindrical end mill cutter for insertion in and sliding engagement with said at least one guide in said guide block adjacent a respective medial and lateral condyle for milling said medial or lateral condyles, said end mill having a radially extending guide surface for engaging said stop surface on said guide block to permit milling of said condyles to a predetermined depth.

4. An apparatus for milling a distal femur as set forth in claim 3 further comprising at least one spacer for insertion between said guide surface on said end mill and said stop surface on said milling guide block to vary the predetermined depth of said milling of said condyles.

* * * * *